(12) United States Patent
Goldstein et al.

(10) Patent No.: US 10,610,828 B2
(45) Date of Patent: Apr. 7, 2020

(54) APPARATUS AND METHOD FOR CLEANING STERILIZER EXHAUST GAS

(71) Applicant: Replacement Parts Industries, Inc., Chatsworth, CA (US)

(72) Inventors: Philip Goldstein, Reseda, CA (US); Randall Hunt, Moorpark, CA (US)

(73) Assignee: Replacement Parts Industries, Inc., Chatsworth, CA (US)

( * ) Notice: Subject to any disclaimer, the term of this patent is extended or adjusted under 35 U.S.C. 154(b) by 0 days.

(21) Appl. No.: 16/253,277

(22) Filed: Jan. 22, 2019

(65) Prior Publication Data
US 2019/0224622 A1    Jul. 25, 2019

Related U.S. Application Data

(60) Provisional application No. 62/619,403, filed on Jan. 19, 2018.

(51) Int. Cl.
| | |
|---|---|
| *B01D 53/86* | (2006.01) |
| *B01D 46/00* | (2006.01) |
| *B01D 39/12* | (2006.01) |
| *B01D 39/14* | (2006.01) |
| *A61L 9/04* | (2006.01) |
| *B01D 53/00* | (2006.01) |

(52) U.S. Cl.
CPC ............ *B01D 53/8671* (2013.01); *A61L 9/04* (2013.01); *B01D 39/12* (2013.01); *B01D 39/14* (2013.01); *B01D 46/003* (2013.01); *A61L 2209/135* (2013.01); *B01D 53/002* (2013.01); *B01D 2255/209* (2013.01); *B01D 2255/2073* (2013.01); *B01D 2255/20738* (2013.01); *B01D 2255/65* (2013.01); *B01D 2255/9202* (2013.01); *B01D 2255/9205* (2013.01); *B01D 2257/70* (2013.01); *B01D 2257/93* (2013.01); *B01D 2258/02* (2013.01); *B01D 2275/10* (2013.01)

(58) Field of Classification Search
None
See application file for complete search history.

(56) References Cited

U.S. PATENT DOCUMENTS 2,836,570 A * 5/1958 Peers .................. C01B 13/0214
502/227
6,488,902 B1 12/2002 DeCato et al.

FOREIGN PATENT DOCUMENTS

CN        104127904 A   *  11/2014

OTHER PUBLICATIONS

Yi et al. CN104127904A—translated document (Year: 2014).*
Yi et al. CN104172904A—translated document (Year: 2014).*

* cited by examiner

*Primary Examiner* — Walter D. Griffin
*Assistant Examiner* — Jelitza M Perez
(74) *Attorney, Agent, or Firm* — Reed Smith LLP

(57) ABSTRACT

An apparatus for cleaning exhaust gas. The apparatus includes a housing having an upstream end configured to receive exhaust gas and a downstream end configured to release the exhaust gas. At least one coalescing filter layer and a catalyst filter layer are disposed within the housing. The catalyst filter layer includes molded sintered pellets formed from a porous material and a non-precious metal catalyst. The molded sintered pellets create a porous area for coalescing oil mist, and the catalyst hydrogen peroxide.

13 Claims, 2 Drawing Sheets

# APPARATUS AND METHOD FOR CLEANING STERILIZER EXHAUST GAS

CROSS-REFERENCE TO RELATED APPLICATION

This application claims the benefit under 35 U.S.C. § 119(e) of the earlier filing date of U.S. Provisional Application No. 62/619,403 filed on Jan. 19, 2018, the disclosure of which is incorporated by reference herein.

BACKGROUND

The present application relates generally to cleaning exhaust gas. In particular, the present application relates to the sterilization of objects using hydrogen peroxide vapor and for the decomposing of hydrogen peroxide vapor exhausted during the process. Systems are available for the sterilization of objects, such as medical instruments, utilizing hydrogen peroxide vapor to effect sterilization. In such systems, the objects are placed in a sterilization chamber and hydrogen peroxide vapor is pumped in. After the objects are sterilized, exhaust comprising hydrogen peroxide vapor is exhausted from the chamber. A need exists for reducing the concentration of hydrogen peroxide exhausted from the system.

SUMMARY OF THE INVENTION

Disclosed herein is a catalytic converter apparatus and method. The catalytic converter is comprised of different media to act as a sorb for oil mist and a catalyst for converting hydrogen peroxide into water and oxygen. The different media are disposed in a plurality of component layers within a housing through which exhaust comprising hydrogen peroxide vapor and possibly oil mist is passed prior to being emitted to the atmosphere. The component layers are not required to be coated with a precious metal catalyst.

BRIEF DESCRIPTION OF THE DRAWINGS

Various embodiments of the invention are described herein in by way of example in conjunction with the following figures, wherein like reference characters designate the same or similar elements.

DETAILED DESCRIPTION OF THE INVENTION

Figure 1:
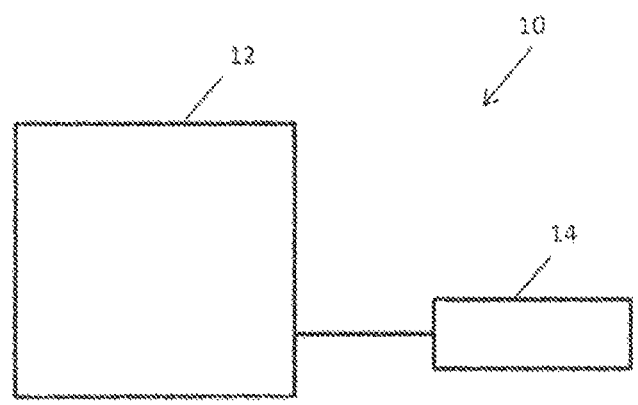
FIG. 1 depicts a block diagram of a sterilization system employing the catalytic converter according to an embodiment of the invention.

As shown in FIG. 1, a sterilization system 10 includes a sterilization chamber 12. Exhaust from sterilization chamber 12 is pumped by a vacuum pump (not shown) into a catalytic converter 14 before being exhausted into the atmosphere. The exhaust may include hydrogen peroxide vapor from the sterilization process and oil mist from lubricating oil for the vacuum pump.

Figure 2:
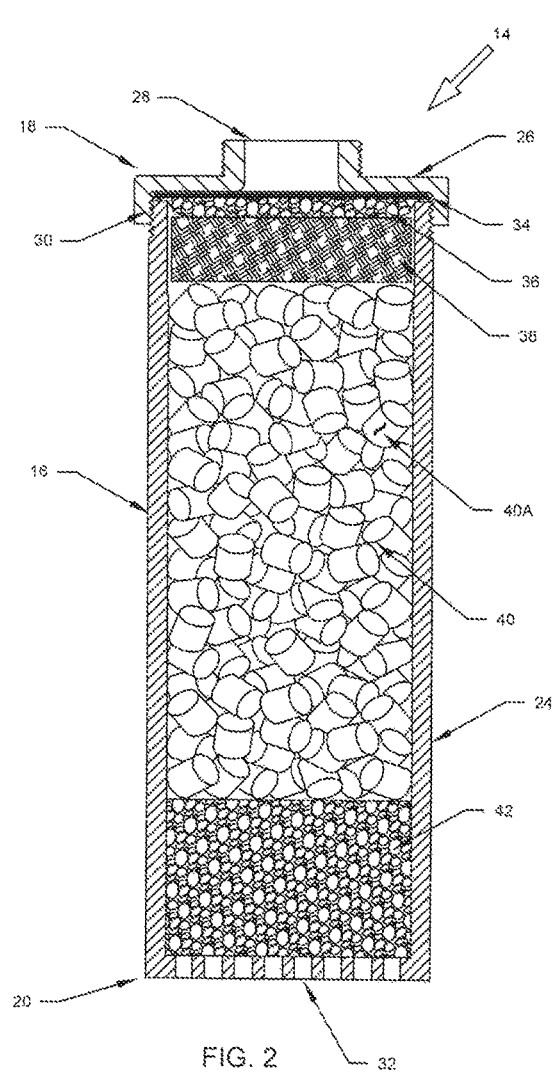
FIG. 2 depicts an assembled cross-section view of the catalytic converter according to an embodiment of the invention.
Figure 3:
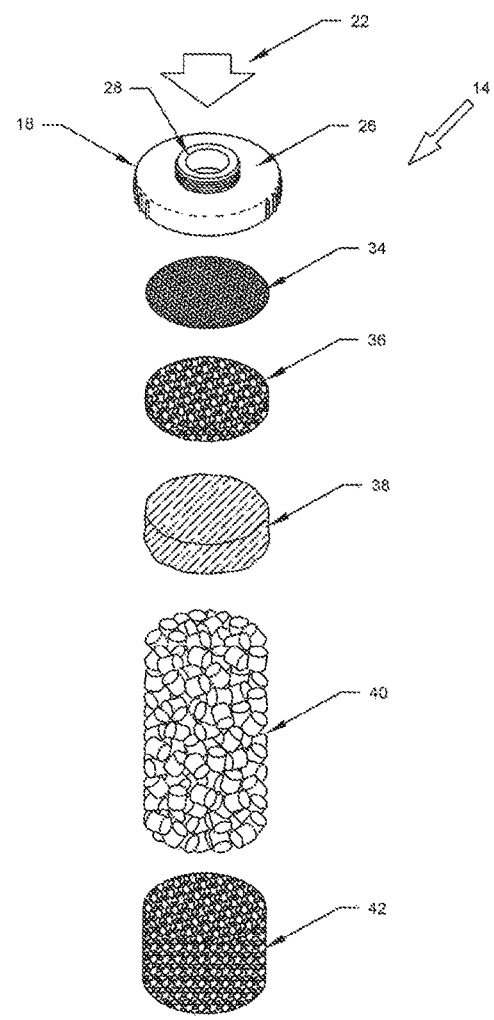
FIG. 3 depicts an exploded view of the catalytic converter according to an embodiment of the invention.
Figure 3:
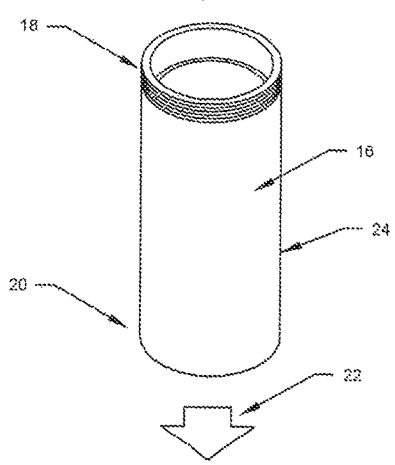

As shown in FIGS. 2 and 3, catalytic converter 14 comprises a plurality of component layers disposed within a housing 16 having an upstream end 18 and a downstream end 20 with respect to a direction of exhaust flow 22. Housing 16 comprises a cylindrical outer portion 24 and an end cap 26 disposed at upstream end 18. End cap 26 has an inlet 28 configured to allow exhaust from sterilization chamber 12 flow into and through the component layers disposed within housing 16. As shown in FIG. 3, end cap 26 comprises a threaded joint 30 joining end cap 26 to housing 16. The downstream end 20 of housing comprises an integral exhaust grate 32. Housing 16, end cap 26 and integral exhaust grate 32 are made from, for example, polyvinyl chloride (PVC) or other suitable materials.

In order, from the upstream end to the downstream end of housing, the component layers comprise one layer of each of the following components: a mesh layer 34, a first foam layer 36, a metal wool layer 38, a filter layer 40, and a second foam layer 42.

Mesh layer 34 is of a suitable size, such as a 40×40 mesh, to screen any potential particle/debris backflow into the vacuum pump. The mesh layer 34 may be made of stainless steel or other suitable materials.

First foam layer 36, metal wool layer 38 and second foam layer 42 act as coalescing filters to capture oil mist exhausting from the vacuum pump. The first and second foam layers 36, 42 are preferably formed from reticulated foam having a dimensional latticework of interconnected ligaments forming a porous, open-celled sponge-like structure. Other suitable foam materials may also be used. First foam layer 36 also functions as a cushion between mesh layer 34 and metal wool layer 38. Foam layer 42 also acts as the base foundation to support and cushion filter layer 40. Metal wool layer 38 is preferably made from aluminum, but may also be made from other suitable materials such as stainless steel.

Filter layer 40 is made of sintered porous pellets 40a (FIG. 4) of a porous material mixed with an inorganic, non-precious metal catalyst. The porous material may be a polyolefin such as ultra-high molecular weight polyethylene (UHMW-PE), but could be made from other suitable porous materials such as suitable metals, ceramics and glass. The inorganic, non-precious metal catalyst is preferably manganese dioxide but could also be other suitable inorganic, non-precious metal catalysts such as lead oxide, andiron (III) oxide. The pellets 40a serve two functions: 1) the pellets 40a are loosely assembled in random fashion inside housing 16 which creates a large porous surface area for coalescing oil mist, and 2) the inorganic, non-precious metal catalyst decomposes hydrogen peroxide by creating a chemical reaction when it comes in contact with hydrogen peroxide vapor. The chemical reaction caused by the inorganic, non-precious metal catalyst results in water and oxygen as the byproducts which are safe to exhaust into the environment.

Figure 4:
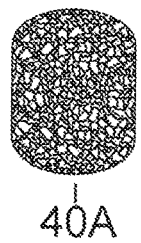
FIG. 4 depicts a front view of a pellet according to an embodiment of the invention.

As shown in FIGS. 2-4, the pellets 40a are porous and cylindrically shaped. The pellets have a porosity in the range of, for example, 30-70% of void in the pellets, and more preferably 50-70% of void in the pellets. The pellets further have a filtration range of, for example, of 100-200 microns. When loosely assembled inside housing 16, the cylindrical shape of the pellets 40a prevents the pellets 40a from being tightly packed. This causes numerous spaces or pores to be present between the pellets 40a. The porosity of the pellets 40a, the large surface area of the numerous pellets 40a and the numerous spaces in between the pellets 40a create an area allowing for coalescing oil mist and hydrogen peroxide vapor to pass through and decompose. In one embodiment, the pellets are approximately 0.25+/−0.005 inches in diameter by 0.25+/−0.005 inches long filling a space of approximately 15 cubic inches. Specifically, in this example, the volume of the housing where the pellets are contained between the second foam layer 42 and the metal wool layer 38 is 15.81 cubic inches. The total volume of the pellets 40a is 9.225 cubic inches, leaving 6.585 cubic inches void. The pellets 40a may have other suitable shapes and dimensions which prevent the pellets 40a from being tightly packed as long as they create a large porous surface area for coalescing oil mist.

The component layers are not required to be coated with a precious metal catalyst and precious metal is not required to be used in the construction of the components. Each component layer when assembled can be in contact with the components next to it and the inside diameter of the cylindrical portion 24 of housing 16 as shown in FIG. 2. The component layers do not require bores through them in order for gases and water to flow through them.

It will be appreciated by those of ordinary skill in the art that the disclosed apparatus may be comprised of a wide and equivalent range of apparatus and components and nothing herein is intended to limit the scope of the disclosed inventions or any embodiments thereof.

We claim:

1. An apparatus for cleaning exhaust gas comprising:
a housing having an upstream end configured to receive exhaust gas and a downstream end configured to release the exhaust gas;
at least one coalescing filter layer disposed within the housing;
a catalyst filter layer disposed within the housing, the catalyst filter layer comprising molded sintered porous pellets comprising a porous material and a non-precious metal catalyst, wherein the molded sintered porous pellets create a porous area for coalescing oil mist, and for decomposing hydrogen peroxide, wherein the porous material is a polyolefin.

2. The apparatus of claim 1, wherein the polyolefin is ultra-high molecular weight polyethylene (UHMW-PE).

3. The apparatus of claim 1,
wherein the non-precious metal catalyst is manganese dioxide.

4. The apparatus of claim 1,
wherein the non-precious metal catalyst is selected from the group consisting of lead oxide and iron oxide.

5. An apparatus for cleaning exhaust gas comprising:
a housing having an upstream end configured to receive exhaust gas and a downstream end configured to release the exhaust gas;
at least one coalescing filter layer disposed within the housing;
a catalyst filter layer disposed within the housing, the catalyst filter layer comprising molded sintered porous pellets comprising a porous material and a non-precious metal catalyst, wherein the molded sintered porous pellets create a porous area for coalescing oil mist, and for decomposing hydrogen peroxide, further comprising a screening layer, wherein the screening layer is upstream of the at least one coalescing filter layer and the catalyst filter layer.

6. An apparatus for cleaning exhaust gas comprising:
a housing having an upstream end configured to receive exhaust gas and a downstream end configured to release the exhaust gas;
at least one coalescing filter layer disposed within the housing;
a catalyst filter layer disposed within the housing, the catalyst filter layer comprising molded sintered porous pellets comprising a porous material and a non-precious metal catalyst, wherein the molded sintered porous pellets create a porous area for coalescing oil mist, and for decomposing hydrogen peroxide;
a screening layer, wherein the screening layer is upstream of the at least one coalescing filter layer and the catalyst filter layer;
wherein the screening layer comprises stainless steel mesh.

7. An apparatus for cleaning exhaust gas comprising:
a housing having an upstream end configured to receive exhaust gas and a downstream end configured to release the exhaust gas;
at least one coalescing filter layer disposed within the housing;
a catalyst filter layer disposed within the housing, the catalyst filter layer comprising molded sintered porous pellets comprising a porous material and a non-precious metal catalyst, wherein the molded sintered porous pellets create a porous area for coalescing oil mist, and for decomposing hydrogen peroxide, wherein the at least one coalescing filter layer comprises at least one foam layer.

8. An apparatus for cleaning exhaust gas comprising:
a housing having an upstream end configured to receive exhaust gas and a downstream end configured to release the exhaust gas;
at least one coalescing filter layer disposed within the housing;
a catalyst filter layer disposed within the housing, the catalyst filter layer comprising molded sintered porous pellets comprising a porous material and a non-precious metal catalyst, wherein the molded sintered porous pellets create a porous area for coalescing oil mist, and for decomposing hydrogen peroxide;
wherein the at least one coalescing filter layer comprises at least one foam layer;
wherein the at least one foam layer comprises a first foam layer disposed upstream of the catalyst filter layer and a second foam layer disposed downstream of the catalyst filter layer.

9. The apparatus of claim 8, wherein the first and second foam layers are composed of reticulated foam.

10. The apparatus of claim 8, wherein at least one coalescing filter layer further comprises a metal wool layer disposed between the first foam layer and the catalyst filter layer.

11. The apparatus of claim 10, wherein the metal wool layer is composed of aluminum wool.

12. An apparatus for cleaning exhaust gas comprising:
a housing having an upstream end configured to receive exhaust gas and a downstream end configured to release the exhaust gas;
at least one coalescing filter layer disposed within the housing;
a catalyst filter layer disposed within the housing, the catalyst filter layer comprising molded sintered porous pellets comprising a porous material and a non-precious metal catalyst, wherein the molded sintered porous pellets create a porous area for coalescing oil mist, and for decomposing hydrogen peroxide, wherein the housing further comprises an end cap.

13. An apparatus for cleaning exhaust gas comprising:
a housing having an upstream end configured to receive exhaust gas and a downstream end configured to release the exhaust gas;
at least one coalescing filter layer disposed within the housing;
a catalyst filter layer disposed within the housing, the catalyst filter layer comprising molded sintered porous pellets comprising a porous material and a non-precious metal catalyst, wherein the molded sintered porous pellets create a porous area for coalescing oil mist, and for decomposing hydrogen peroxide, wherein the downstream end of the housing comprises an integral exhaust grate.

* * * * *